United States Patent [19]
Johnson

[11] Patent Number: 5,941,858
[45] Date of Patent: Aug. 24, 1999

[54] MEDICAL DEVICE FOR INSERTION INTO THE BODY

[75] Inventor: Theodore A. Johnson, St. Paul, Minn.

[73] Assignee: Sims Deltec, Inc., St., Minn.

[21] Appl. No.: 08/932,287

[22] Filed: Sep. 17, 1997

Related U.S. Application Data

[63] Continuation of application No. 08/281,780, Jul. 28, 1994, Pat. No. 5,669,383.

[51] Int. Cl.$^6$ .................................................. A61M 25/00
[52] U.S. Cl. .......................... 604/282; 604/264; 600/423; 600/434; 600/435
[58] Field of Search ..................... 607/282, 280, 607/264, 93; 600/12, 13, 14, 433–435, 431, 407, 409–411, 420, 421, 423, 550; 324/219, 220

[56] References Cited

U.S. PATENT DOCUMENTS

| | | |
|---|---|---|
| 3,618,613 | 11/1971 | Schulte . |
| 3,720,209 | 3/1973 | Bolduc . |
| 3,968,725 | 7/1976 | Holzhauer . |
| 4,173,228 | 11/1979 | Van Steenwyk et al. . |
| 4,321,854 | 3/1982 | Foote et al. . |
| 4,634,432 | 1/1987 | Kocak . |
| 4,905,698 | 3/1990 | Strohl, Jr. et al. . |
| 4,939,317 | 7/1990 | Hostler . |
| 4,952,357 | 8/1990 | Euteneuer . |
| 4,957,110 | 9/1990 | Vogel et al. . |
| 4,967,753 | 11/1990 | Hasse et al. . |
| 4,985,022 | 1/1991 | Fearnot et al. . |
| 5,005,592 | 4/1991 | Cartmell . |
| 5,016,646 | 5/1991 | Gotthardt et al. . |
| 5,069,674 | 12/1991 | Fearnot et al. . |
| 5,104,966 | 4/1992 | David . |
| 5,115,814 | 5/1992 | Griffith et al. . |
| 5,178,158 | 1/1993 | de Toledo . |
| 5,226,423 | 7/1993 | Tenerz et al. . |
| 5,275,597 | 1/1994 | Higgins et al. . |
| 5,386,828 | 2/1995 | Owens et al. . |
| 5,405,338 | 4/1995 | Kranys . |
| 5,423,773 | 6/1995 | Jimenez . |
| 5,423,774 | 6/1995 | Fischell et al. . |
| 5,450,853 | 9/1995 | Hastings et al. . |
| 5,669,383 | 9/1997 | Johnson ................................ 604/264 |

FOREIGN PATENT DOCUMENTS

| | | |
|---|---|---|
| 0 358 117 | 3/1990 | European Pat. Off. . |
| 0 370 785 | 5/1990 | European Pat. Off. . |
| 93 20750 | 10/1993 | WIPO . |

Primary Examiner—Ronald Stright, Jr.
Attorney, Agent, or Firm—Merchant, Gould, Smith, Edell, Welter & Schmidt, P.A.

[57] ABSTRACT

A catheter apparatus for use in determining the location of a tip of a catheter inside biological tissue is disclosed. The apparatus includes a catheter, a detector positioned within the catheter, and a polyimide sheath containing the detector and forming a detector assembly. The sheath is comprised of a first member, a polyimide layer, and a second member having an undulating outer surface sandwiched therebetween. The detector assembly may be removed from the catheter without damage thereto once the tip of the catheter is in its desired location inside biological tissue.

6 Claims, 2 Drawing Sheets

MEDICAL DEVICE FOR INSERTION INTO THE BODY

This is a Continuation of application Ser. No. 08/281,780, filed Jul. 28, 1994, now U.S. Pat. No. 5,669,383 which application(s) are incorporated herein by reference.

BACKGROUND OF THE INVENTION

Catheters are tubular medical devices which, when inserted into canals, vessels, passageways and the like of a human or animal, permit injection or withdrawal of fluids. In several applications, such as parenteral nutrition, cancer chemotherapy, and frequent antibiotic therapy, the correct placement of the tip of the catheter is essential. As a result, the prior art provides for methods and devices to accurately determine the location of the tip of a catheter within a patient's body. One such method and device for detecting the tip of a catheter is disclosed in U.S. Pat. No. 4,905,698 to Strohl, Jr. et al., the disclosure of which is incorporated herein by reference.

In general, the Strohl method and device utilizes a source which generates an alternating magnetic field, and a detector positioned proximate the distal end of the catheter. The detector generates a voltage in response to the proximity of the field generated by the source. The phase of the voltage in the detector shifts as the source passes over it. By referencing anatomical landmarks at the time the phase shift occurs, the caregiver can determine the exact location of the detector, and thus the location of the tip of the catheter.

The detector consists of a magnetic core and a pair of leads that are wrapped around the core and fed through the lumen of the catheter to a power source. The magnetic core and leads are housed within a protective sheath to form a detector assembly. When an electric current passes through the leads, the position of the distal end of the catheter may be located. Once the tip of the catheter is properly positioned, the detector assembly may be removed.

As the detector assembly is removed from the catheter, it is subject to various forces. There is, of course, the pulling force applied by the caregiver as he or she pulls on the sheath to remove the detector assembly from the catheter. In particular, the sheath is subject to frictional forces exerted by the inner walls of the catheter as the detector assembly is withdrawn therefrom. As the caregiver pulls on the detector assembly, the sheath elongates while the leads of the detector tighten. Depending on the amount of force used by the caregiver, the leads of the detector can snap, thereby making the detector inoperable. In some cases, such as when the catheter is placed in tortious configurations within the patient's body, the caregiver must twist and turn the sheath. As a result, the force necessary to remove the detector assembly under such hard extractions may cause damage not only to the detector, but also to the sheath. The sheath is also subject to forces resulting from the physical compression associated with the placement of the catheter into a patient's body. Consequently, the sheath material and its structural configuration must possess frictional, tensile, and flexibility properties to withstand such forces and thus, prevent it and the detector from being damaged when removed from the catheter. As a result, the selection of the sheath material and its structural configuration are critical.

One of the commonly used materials for sheaths in the past was polyethylene. While polyethylene is compatible with the recently emerging polyurethane catheters, it is not compatible with conventional silicone catheters. When a polyethylene sheath is used with a silicone catheter, the polyethylene tends to bind on the silicone. This binding effect makes it extremely difficult to remove the detector assembly from the catheter without causing damage thereto. Silicone catheters, however, are desirable since they possess elastic properties that are compatible with the functions required to be performed by the catheter within the body.

Polyethylene has several other shortcomings. First, polyethylene does not have the tensile strength necessary to withstand the forces required to pull the detector assembly out of the catheter. Second, a polyethylene sheath often cannot withstand the forces resulting from the physical interactions associated with the placement of the catheter into a patient's body. Consequently, polyethylene has not proven very effective for sheaths, especially when used with silicone catheters.

A disadvantage with existing sheaths regardless of their material makeup is their generally flat outer surface configuration. While such a configuration is simple and thus inexpensive to manufacture, it inhibits the removal of the detector assembly by increasing the amount of contact between the outer surface of the sheath and the inner walls of the catheter. As a result, more force must be applied to the detector assembly in order to remove it from the catheter. The risk of sheath and detector breakage is thus further increased.

The above-mentioned shortcomings of existing sheaths also present financial concerns. Hospitals and like facilities must keep excess inventory of detector assemblies in order to account for the high potential for damaged detectors and/or sheaths. Moreover, when a detector assembly is damaged, the catheter must also be removed and discarded regardless of whether or not it has, in fact, been damaged. As a result, an excess inventory of catheters must also be maintained. A typical catheter and detector assembly can cost about $150.00 (U.S. Dollars). In the case of more sophisticated catheters, such as those having implantable reservoirs, the costs can often exceed about $500.00 (U.S. Dollars). In an average-sized medical facility, even a low damage rate can be quite costly. In light of the heightened awareness to reduce healthcare costs, such waste is unacceptable.

The disadvantages associated with existing sheaths, however, are not solely economical. The insertion and removal of a catheter can be quite painful and discomforting to the patient. More importantly, breakage of the sheath can be life threatening. For example, broken pieces of the detector may travel down the catheter and migrate into the patient's vascular stream. It is possible that the caregiver may need to perform surgery to remove the broken pieces. In terms of providing a high standard of patient care, the minimization of insertions and removals of the catheter and of surgery is critical. This is especially true in light of the increased competition among doctors and medical facilities.

Accordingly, there is a need for a catheter apparatus that allows for safe and easy removal of a detector from the lumen of a catheter.

SUMMARY OF THE INVENTION

A catheter apparatus for use in determining the location of a tip of a catheter inside biological tissue is disclosed. The apparatus includes a catheter defining a lumen, a detector positioned within the lumen of the catheter, and a polyimide sheath attached to an exterior of the detector to form a detector assembly. The detector assembly is adapted to be removed from the catheter without damage thereto when the tip of the catheter is in a desired location inside biological tissue.

A sheath apparatus for use in such a device is also disclosed. The sheath apparatus includes a first sealing member defining a passageway in which to house the detector, and a second member communicating over substantially the entire length of the first member and supported by the first member. The second member has a polyimide coating deposited thereover. In another aspect of the invention, the sheath apparatus includes a flexible member defining a passageway and having an undulating outer surface adapted to increase the overall surface area of the flexible member, and a polyimide coating deposited over the flexible member.

A method of positioning a catheter tip inside biological tissue using a catheter detector having a sheath assembly including a polyimide construction is also disclosed.

DETAILED DESCRIPTION OF THE PREFERRED EMBODIMENTS

Figure 1:
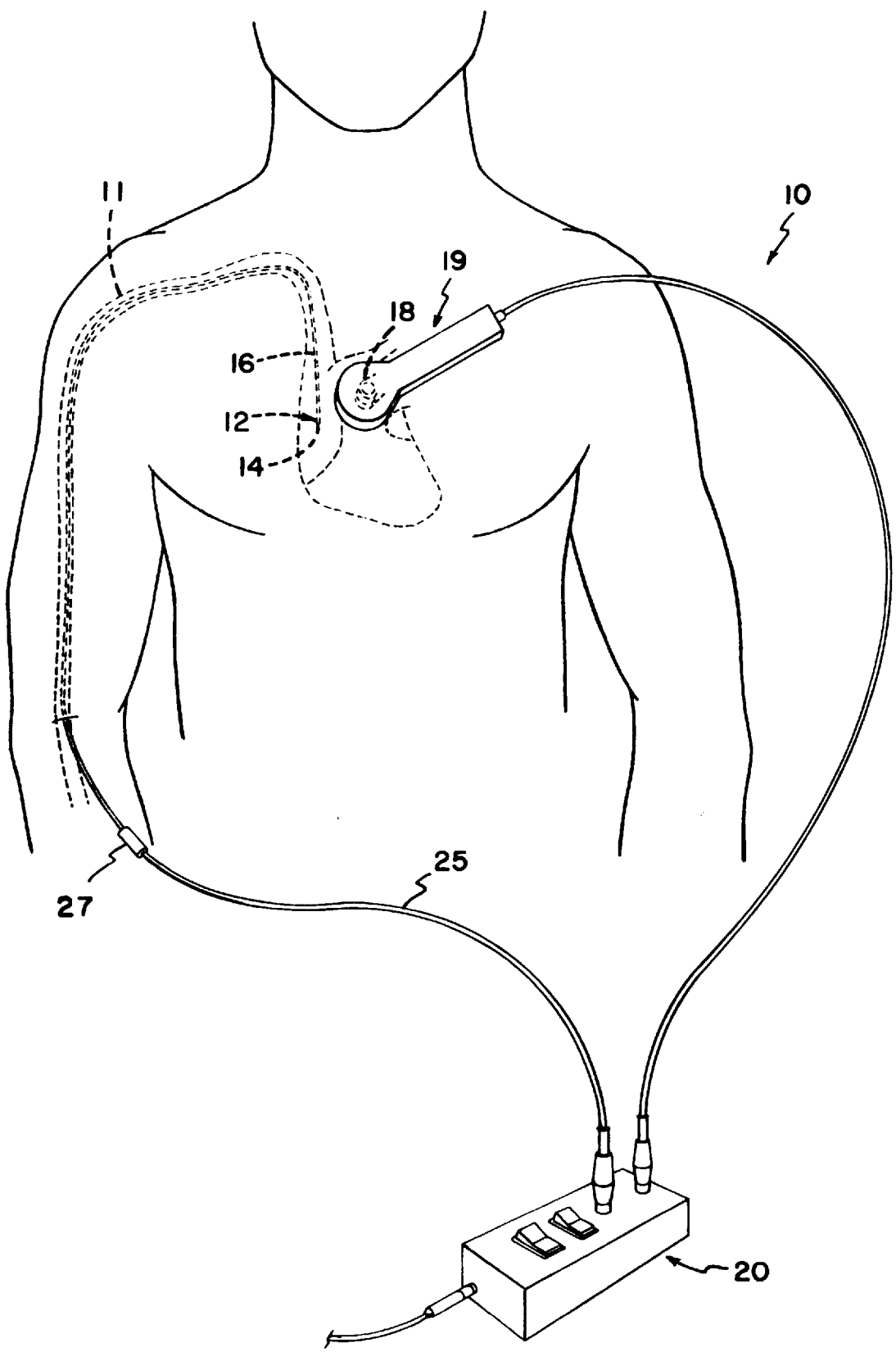
FIG. 1 is a front view of an apparatus for determining the location of a catheter inside a patient's body.

An apparatus 10 for determining the location of the tip 14 of a catheter 16 inside biological tissue is shown in FIG. 1. The catheter shown in FIG. 1 is an arm-placed catheter implanted through a tunnel 11 bored within the arm of the patient. It can be understood by those skilled in the art, however, that apparatus 10 may be used with other types of catheters, such as chest catheters, percutaneous catheters or catheters which are part of an implantable access system within the veins or arteries of a patient.

With initial reference to FIG. 1, apparatus 10 includes an alternating current (AC) electromagnetic energy field pick up detector 12 positioned within catheter 16, a locator 19 containing an AC electromagnetic energy source 18, and an electronic controller 20 to which detector 12 and locator 19 are connected. As can be better seen in FIG. 2, catheter 16 defines a lumen within which detector 12 is contained. Detector 12 is further enclosed within a protective sheath 22 to form a detector assembly. Sheath 22 is preferably positioned within catheter 16 so that detector 12 is aligned with tip 14 of catheter 16. In a preferred form, a clearance 21 is provided between sheath 22 and the inner walls of catheter 16 to help in the unencumbered removal of the detector assembly from catheter 16.

Detector 12 includes a generally cylindrical core 24 formed of magnetically permeable material. Core 24 extends into the free end of sheath 22 and is suitably secured thereto, such as by adhesive located between the inside surface of sheath 22 and the outer surface of core 24.

Core 24 extends to the free end of sheath 22 and includes a lead 28 wound thereon coaxially with sheath 22. Lead 28 includes a first end and a second end, both of which extend through the lumen of sheath 22 and connect to controller 20 via a standard electrical cable 25 through a junction box 27 (See FIG. 1). Catheter 16 and sheath 22 may include standard positioning connectors utilized in standard catheter placement techniques.

Figure 2:
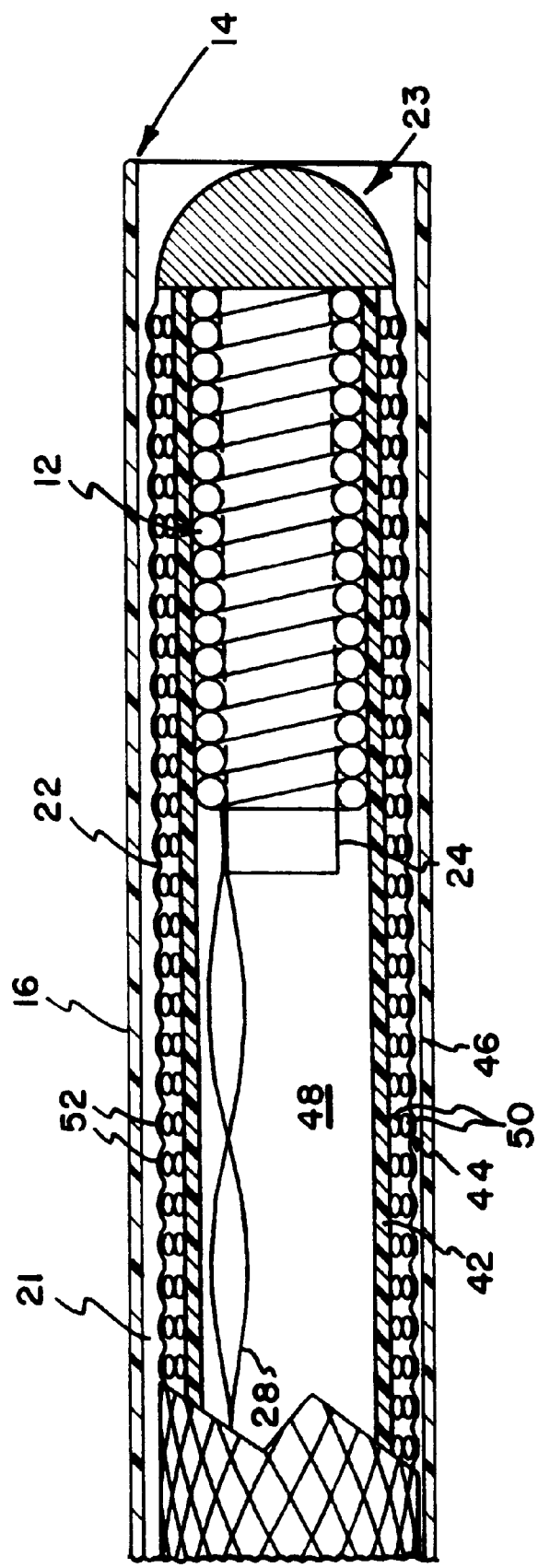
FIG. 2 shows an enlarged cross sectional view of the distal portion of the catheter as shown in FIG. 1.

As can be seen in FIG. 2, sheath 22 includes a first member 42 and a second member 44 communicating over substantially the entire length of first member 42. Sheath 22 has a tip 23 at one end which is preferably aligned with tip 14 of catheter 16. Tip 23 preferably is a U.V. cure acrylic tip. Sheath 22 runs the entire length of catheter 16 and connects to junction box 27. Before catheter 16 is inserted into the patient's body, sheath 22 and catheter 16 are locked together at the end of sheath 22 opposite tip 23. Once the location of tip 14 of catheter 16 is determined, sheath 22 and catheter 16 are unlocked, thereby permitting removal of detector assembly from catheter 16.

First member 42 defines a passageway 48 in which to house detector 12. First member 42 also acts as a sealant to prevent contamination of detector 12, such as by bodily fluids. First member 42 is preferably made of polyimide and has a thickness of about 0.002 inches (about 0.005 cm). Polyimide is a flexible, non-corrosive material exhibiting a nominal tensile strength of about 20,000 lbs. per square inch (about 138,000 kPa) and an even higher flexural strength. This cross-linked polymer provides sheath 22 with an extremely high tensile strength. In the preferred form, when sheath 22 is pulled 12 inches per minute (about 30.5 cm./minute), it can withstand about 8 lbs. (about 35 Newtons). Other materials are anticipated for first member 42 in accordance with the principles of the invention.

While a polyimide first member 42 provides a high tensile strength to sheath 22, it is not very flexible, and is thus prone to kinking or splitting, especially when bent or flexed around corners. In order to provide flexibility to polyimide first member 42, the thickness of first member 42 would have to be significantly reduced. While reducing the wall thickness helps maintain the sheath's small size, it also reduces the overall strength of first member 42.

The addition of a second member 44 having a unique outer surface configuration maintains the integrity of the polyimide of first member 42 while also providing the requisite flexibility. Second member 44 is composed of at least one wire 50 which is wound in spiral-like manner about first member 42. The tightness of second member 44 in relation to first member 42 is dependent upon the size of first member 42. Second member 44 has a high enough density to protect first member 42 from kinking or splitting, but yet low enough to maintain its flexibility. While second member 44 is preferably made of stainless steel, it can be made of other flexible materials, such as polyester or nylon.

In a preferred form as shown in FIG. 2, second member 44 includes a plurality of wires 50 intertwined and placed over first member 42 to form a braid. Wires 50 have a pitch ranging between 50 to 110 crossovers/inch (about 20 to 43 crossovers/cm.), preferably around 65 crossovers/inch (about 25.5 crossovers/cm.). Every time one of the wires crosses the other wire, a protrusion 52 is created. The overall contact between the outer surface of sheath 22 and the inner surface of catheter 16 is therefore limited to protrusions 52. As a result, there is less friction between the two surfaces, thereby reducing the force necessary to pull the detector assembly out of catheter 16. Depending on the pitch at which wires 50 are wound, the braided configuration can provide two to three times the strength of that of a second member which is not braided. In a preferred form, second member 44 is composed of about 16 to 32 wires having a thickness of about 0.003 inches (about 0.007 cm) at each protrusion and configured such that only about 50% of the outer surface of second member 44 contacts the inner walls of catheter 16.

Second member 44 includes a polyimide outside surface 46. Second member 44 is preferably dipped one or more times in a liquid coating of polyimide solution, which is dried between coats to build up a protective outer layer of desired thickness and texture. The outer layer, however, should be thin enough to retain the unique undulating surface configuration so as to achieve the benefits of the reduced contact between sheath 22 and catheter 16. In a preferred form, outside surface 46 is about 0.002 inches (about 0.005 cm) thick. This polyimide outside surface or exterior coating prevents sheath 22 from sticking to or binding on the inner walls of catheter 12. It also acts as a dielectric so as to prevent lead 28 from conducting into the patient's body. As assembled, sheath 22 is preferably about 0.009 inches (about 0.023 cm.) thick.

Source 18 is positionable on the patient's skin at an external anatomical landmark consistent with the desired end-point location of catheter tip 14. Source 18 is connected to controller 20 and develops and transmits an AC magnetic field. Detector 12 reacts to the AC magnetic field transmitted by source 18 by generating a small voltage when in physical proximity to source 18. The phase of the voltage generated by detector 12 shifts as locator 19 passes over detector 12. By referencing anatomical landmarks at the time the phase shifts occur, the caregiver can determine the location of detector 12, and thus the location of tip 14 of catheter 12. Once the location of catheter tip 14 is determined, the detector assembly may be removed. The detector assembly is removed from the lumen of catheter 12 by unlocking the detector assembly and catheter 16 and pulling on the detector assembly until it is completely removed from catheter 16.

While the foregoing detailed description of the present invention describes the invention of the preferred embodiments, it will be appreciated that it is the intent of the invention to include all modifications and equivalent designs. Accordingly, the scope of the present invention is intended to be limited only by the claims which are appended hereto.

What is claimed is:

1. A medical device for insertion into the body comprising:

a polyimide first member having a tube shape with an internal passageway and an open end;

an elongated strengthening member surrounding the polyimide first member;

a polyimide coating surrounding the elongated strengthening member and the polyimide first member; and a tip positioned in the open end of the polyimide first member to close off the open end.

2. The medical device of claim 1, wherein the polyimide first member, the elongated strengthening member, the polyimide coating and the tip form a unitary device, and further comprising a catheter defining a lumen, the unitary device positioned within the lumen of the catheter.

3. The medical device of claim 2, wherein the catheter comprises silicone.

4. The medical device of claim 1, wherein the tip includes a U.V. cure acrylic material.

5. The medical device of claim 1, further comprising a detector positioned in the internal passageway of the polyimide first member adjacent to the tip.

6. The medical device of claim 1, wherein the elongated strengthening member includes a metallic wire braid wrapped around the polyimide first member.

* * * * *